United States Patent [19]

Chaykovsky et al.

[11] Patent Number: 5,262,544
[45] Date of Patent: Nov. 16, 1993

[54] 5,7-DINITRO-5,7-DIAZA-1,3-DIOXABICY-CLO(3:3:0)OCTAN-2-ONE

[75] Inventors: Michael Chaykovsky, Columbia; William M. Koppes, Adelphi, both of Md.

[73] Assignee: The United States of America as represented by the Secretary of the Navy, Washington, D.C.

[21] Appl. No.: 59,929

[22] Filed: May 10, 1993

[51] Int. Cl.$^5$ ............................................ C07D 235/02
[52] U.S. Cl. ................................................. 548/303.1
[58] Field of Search ...................................... 548/303.1

[56] References Cited

U.S. PATENT DOCUMENTS 4,544,635 10/1985 Ohashi et al. .................... 548/303.1

Primary Examiner—Mary C. Lee
Assistant Examiner—Joseph K. McKane
Attorney, Agent, or Firm—John D. Lewis; Roger D. Johnson

[57] ABSTRACT 5,7-Dinitro-5,7-diaza-1,3-dioxabicyclo[3:3:0] octan-2-one is an explosive which is comparable in energy (detonation pressure) to RDX but which has an impact sensitivity comparable to TNT. It is prepared by condensing one mole of methylenedinitramine with one mole of 4,5-dichloro-1,3-dioxolan-2-one.

1 Claim, No Drawings

5,7-DINITRO-5,7-DIAZA-1,3-DIOXABICYCLO(3:3:-0)OCTAN-2-ONE

BACKGROUND OF THE INVENTION

This invention relates to explosives and more particularly to organic nitramine explosives.

A common problem with high energy explosives is that they have low shock and thermal stabilities. One approach to ameliorate the sensitivity characteristics of highly energetic but sensitive explosives such as RDX and HMX is to embed the explosive in elastomeric polymer binders. While this reduces the shock and thermal sensitivities, it also lowers the energy content of the explosive composites proportionally. Another approach is to use less sensitive explosive compounds such as symtriaminotrinitrobenzene (TATB) or nitroguanidine. However, these compounds have lower energy contents that are only comparable to TNT. As a result, their usefulness is limited.

It would be desirable to provide a compound that combines high energy with good shock and thermal stabilities.

SUMMARY OF THE INVENTION

Accordingly, an object of this invention is to provide a new energetic compound.

Another object of this invention is to provide a new explosive compound.

A further object of this invention is to provide a new energetic explosive compound having good thermal and shock stabilities.

These and other objects of this invention are accomplished by providing 5,7-dinitro-5,7-diaza-1,3-dioxabicyclo[3:3:0]octan-2-one.

DETAILED DESCRIPTION OF THE PREFERRED EMBODIMENT 5,7-Dinitro-5,7-diaza-1,3-dioxabicyclo[3:3:0]octan-2-one is a new energetic compound which is suitable as a substitute for RDX (1,3,5-trinitro-1,3,5-triazacyclohexane) to produce less sensitive energetic explosive compositions. A comparison of the important features or properties of 5,7-dinitro-5,7-diaza-1,3-dioxabicyclo[3:3:0]octan-2-one and RDX is presented in the following table:

| Property | RDX | 5,7-dintro-5,7-diaza-1,3-dioxabicyclo[3:3:0]octan-2-one |
|---|---|---|
| Melt. Pt. (°C.) | 204[1] | 210–211 |
| Oxid. Bal. (OB$_{100}$)[2] | 0 | 0 |
| Density (g/cm$^3$) | 1.82[1] | 1.952 |
| Det. Press. (kbar, meas.)[3] | 338 ($\rho$ = 1.767) | |
| Det. Press. (kbar, calcd.)[4] | 344.8 ($\rho$ = 1.806) | 323.4 ($\rho$ = 1.952) |
| Impact Sens. (H$_{50}$, cm)[5] | 19 | 59 |

[1]R. Meyer, "Explosives," Third Ed. VCH Publishers, New York, NY (1987), p. 71.
[2]Calculated by the Method of M.J. Kamlet, Proc. Sixth Symp. (Intern.) Detonation, Coronado (San Diego), CA (1976). ONR Symnposium Report ACR-221, p. 312.
[3]B. M. Dobratz and P. C. Crawford, Lawrence Livermore National Laboratory Handbook, VCRL-52997 Change 2, (1985), p. 19-131.
[4]Calculated by the method of M. J. Kamlet and S. J. Jacobs, J. Chem. Phys. 48, 23 (1968).
[5]Impact sensitivities were measured at NSWC using an ERL Bruceton apparatus; 25 drops per sample; approximately 35 mg per shot; 2.5 kg drop weight; 180A garnet paper; type 12 tools. Under these conditions, the following impact sensitivities were observed. TNT, 78 cm.; PBXN-109, 53 cm.; Comp. C-4, 44 cm.; HMX, 19 cm.; RDX, 19 cm.

As shown in the table, the calculated detonation pressure of 5,7-dinitro-5,7-diaza-1,3-dioxabicyclo[3:3:0]octan-2-one (323.4 kbar) is comparable to the calculated detonation pressure of RDX (344.8 kbar). (Note: the measured detonation pressure of RDX was 338 kbar). However, the impact sensitivity of 5,7-dinitro-5,7-diaza-1,3-dioxabicyclo[3:3:0]octan-2-one (59 cm) is much less than the impact sensitivity of RDX (19 cm). Therefore, 5,7-dinitro-5,7-diaza-1,3-dioxabicyclo[3:3:0 octan-2-one is a dense, energetic, thermally stable explosive which is much safer than RDX and which has the potential to replace RDX in Navy explosive formulations where sensitivity characteristics are of great importance.

The 5,7-dinitro-5,7-diaza-1,3-dioxabicyclo[3:3:0]octan-2-one (III) is prepared by reacting one mole of methylenedinitramine (I) with one mole of 4,5-dichloro-1,3-dioxolan-2-one (II) in a suitable polar solvent such as acetonitrile, $CH_3C \equiv N$, Two molecules of HCl are produced with each mole of the product (III). A suitable base such as triethylamine $(CH_3CH_2)_3N$ is slowly added to the agitated (stirred) reaction mixture to neutralize and remove the HCl as the salt triethylamine hydrogen chloride, $(CH_3CH_2)_3NH^+Cl^-$, and thus help the reaction to proceed to completion. Details of the process are illustrated in the Example.

The general nature of the invention having been set forth, the following example is presented as specific illustration thereof. It will be understood that the invention is not limited to this specific example but is susceptible to various modifications that will be recognized by one of ordinary skill in the art.

EXAMPLE 5,7-dinitro-5,7-diaza-1,3-dioxabicyclo[3:3:0]octan-2-one

A solution of triethylamine (10.1 g, 0.1 mol) in $CH_3CN$ (25 mL) was added dropwise to a stirred solution of methylenedinitramine (6.8 g, 0.05 mol) and 4,5-dichloro-1,3-dioxolan-2-one (9.60 g, 0.052 mol, of 85% technical grade-Aldrich Chem. Co.) in $CH_3CN$ (150 mL), cooled in ice, over 20 minutes. Stirring was continued at 0° C. for 15 minutes and then for 2 hours longer with the bath removed. The mixture was filtered to remove 13.0 g (13.78=theor.) of triethylamine HCl and the filtrate was evaporated to leave a yellow residue of oil and solid. This mixture was dissolved in the minimum amount of warm $CH_3CN$ and placed on a column of silica gel (40 g, EM grade 62). Elution was conducted with 10% $CH_3CN$-benzene until no more organic material appeared in the eluted fractions. The combined fractions were evaporated and the residue was triturated with ethanol and filtered to yield a white solid (830 mg, 7.5%), mp 198°–203° C. (dec.). Recrystallization from $CH_3CN$-isopropyl ether gave colorless prisms: mp 210°–211° C. (dec.); $^1$H NMR (acetone-d$_6$) 7.13 (s, 2, CHs), 6.00 (q, 2, CH$_2$); mass spectrum (CI CH$_4$), m/z (relative intensity) 261 (0.5, M+41), 249 (1, M+29), 221 (7, M+1), 177 (8), 159 (8), 114 (100). Anal. Calcd. for C$_4$H$_4$N$_4$O$_7$: C, 21.83; H, 1.83; N, 25.46.

Found: C, 21.97; H, 1.88; N, 25.26. X-ray crystallographic analysis confirmed the structure and showed a crystal density of 1.952.

Obviously, numerous other modifications and variations of the present invention are possible in light of the foregoing teachings. It is therefore to be understood that within the scope of the appended claims the invention may be practiced otherwise than as specifically described.

What is claimed is:

1. 5,7-dinitro-5,7-diaza-1,3-dioxabicyclo[3:3:0]octan-2-one.

* * * * *